(12) United States Patent
Sambusseti et al.

(10) Patent No.: US 9,393,099 B2
(45) Date of Patent: Jul. 19, 2016

(54) ORTHOTOPIC ARTIFICIAL BLADDER ENDOPROSTHESIS

(71) Applicants: Antonio Sambusseti, Cremona (IT); Gianni Cancarini, Brescia (IT)

(72) Inventors: Antonio Sambusseti, Cremona (IT); Gianni Cancarini, Brescia (IT)

(*) Notice: Subject to any disclaimer, the term of this patent is extended or adjusted under 35 U.S.C. 154(b) by 0 days.

(21) Appl. No.: 14/427,968

(22) PCT Filed: Sep. 17, 2013

(86) PCT No.: PCT/IB2013/058599
§ 371 (c)(1),
(2) Date: Mar. 13, 2015

(87) PCT Pub. No.: WO2014/045190
PCT Pub. Date: Mar. 27, 2014

(65) Prior Publication Data
US 2016/0000552 A1    Jan. 7, 2016

(30) Foreign Application Priority Data
Sep. 19, 2012   (IT) .............................. MI2012A1555

(51) Int. Cl.
*A61F 2/04* (2013.01)

(52) U.S. Cl.
CPC ............. *A61F 2/042* (2013.01); *A61F 2210/00* (2013.01); *A61F 2210/0057* (2013.01); *A61F 2210/0076* (2013.01); *A61F 2220/0075* (2013.01); *A61F 2230/0067* (2013.01); *A61F 2230/0071* (2013.01); *A61F 2230/0093* (2013.01); *A61F 2250/006* (2013.01); *A61F 2250/0025* (2013.01); *A61F 2250/0031* (2013.01); *A61F 2250/0051* (2013.01); *A61F 2250/0054* (2013.01)

(58) Field of Classification Search
CPC ..... A61F 2/042; A61F 2/04; A61F 2002/045; A61F 2/12
See application file for complete search history.

(56) References Cited

U.S. PATENT DOCUMENTS

| | | |
|---|---|---|
| 2002/0007223 A1 | 1/2002 | Matapurkar |
| 2007/0276507 A1 | 11/2007 | Bertram et al. |
| 2008/0319460 A1 | 12/2008 | Cortellini |
| 2011/0270409 A1 | 11/2011 | Sambusseti |
| 2013/0103164 A1 | 4/2013 | Sambusseti |

(Continued)

FOREIGN PATENT DOCUMENTS

| | | |
|---|---|---|
| CN | 101304706 A | 11/2008 |
| CN | 102271621 A | 12/2011 |
| FR | 2116838 A5 | 7/1972 |
| WO | 2007039159 A1 | 4/2007 |
| WO | 2007095193 A2 | 8/2007 |
| WO | 2009077047 A1 | 6/2009 |

(Continued)

OTHER PUBLICATIONS

International Search Report and Written Opinion mailed Jan. 23, 2014 for PCT/IB2013/058599 to Antonio Sambusseti et al. filed Sep. 17, 2013.

*Primary Examiner* — Andrew Iwamaye
(74) *Attorney, Agent, or Firm* — Vorys, Sater, Seymour and Pease LLP

(57) ABSTRACT

An orthotopic artificial bladder endoprosthesis includes a first portion connectable to a urethra of a patient and a second portion connectable to the ureters of the patient; the first portion including a collapsible cover made of a multi-layered silicone membrane having an external surface and an internal surface both coated with pyrolytic turbostratic carbon; the second portion including a resorbable cap including a fabric of PGA fibers and a frame, coupled with the cap, made using PGA/PLA copolymer; the cover and the cap being connected together along their respective edges, to define an enclosure.

16 Claims, 3 Drawing Sheets

(56) References Cited

U.S. PATENT DOCUMENTS

| | | |
|---|---|---|
| 2013/0317622 A1 | 11/2013 | Sambusseti et al. |
| 2014/0012394 A1 | 1/2014 | Sambusseti |
| 2015/0045907 A1* | 2/2015 | Sambusseti ............ A61F 2/042 623/23.65 |
| 2015/0148912 A1* | 5/2015 | Sambusseti ........... A61F 2/0063 623/23.65 |
| 2015/0223924 A1 | 8/2015 | Sambusseti et al. |

FOREIGN PATENT DOCUMENTS

| | | |
|---|---|---|
| WO | 2011018300 A1 | 2/2011 |
| WO | 2011064110 A1 | 6/2011 |
| WO | 2011112626 A1 | 9/2011 |
| WO | 2011137394 A1 | 11/2011 |
| WO | 2011138371 A1 | 11/2011 |
| WO | WO 2011160875 A1 * | 12/2011 |
| WO | WO2013/135543 A1 * | 9/2013 |

* cited by examiner

ORTHOTOPIC ARTIFICIAL BLADDER ENDOPROSTHESIS

CROSS-REFERENCE TO RELATED APPLICATIONS

This is a §371 National Stage Application of International Application No. PCT/IB2013/058599 filed on Sep. 17, 2013, claiming the priority of Italian Patent Application No. MI2012A001555 filed on Sep. 19, 2012.

NOTICE OF INVENTION UNDER JOINT DEVELOPMENT AGREEMENT

The disclosure of US published patent application nos. 2015-0045907 and 2015-0148912 and the claimed invention were made by or on behalf of Antonio Sambusseti and Gianni Cancarini who were the parties to a joint research agreement under 35 U.S.C. 103(c), and the agreement was in effect on or before the effective filing date of the claimed invention, and the claimed invention was made as a result of activities undertaken within the scope of the joint research agreement.

The present invention relates to an orthotopic artificial bladder endoprosthesis.

The application of the present invention lies in the replacement of the bladder of a patient, if the latter is suffering from serious incurable diseases such as to compromise the correct operation thereof.

Known bladder endoprosthesis comprise a balloon casing made with a layered silicone membrane.

This balloon is sufficiently rigid as to keep its shape stably and flexible enough to be able to be compressed manually to ensure that it empties.

The casing has a connection element located in a lower part of the casing to connect with the patient's urethra. Similarly, two connection bodies are located at the top to enable connection with the ureters.

These connections are achieved by suturing or by simply interlocking.

Disadvantageously, known bladder endoprostheses have some drawbacks.

Firstly, the connection of the ureters by means of the connection bodies can in some cases cause problems of stenosis of the ureters.

Furthermore, this type of connection increases the possibility of infections.

In fact, after the replacement operation, a catheter is inserted into the patient's urethra. It is sometimes the case that an infection enters the endoprosthesis via the catheter, making antibiotic treatment necessary.

However, this treatment has reduced effectiveness in the area where the ureters connect with the endoprosthesis because the bacterial load can install itself stably on the artificial material that constitutes the endoprosthesis.

In this context, the technical task at the heart of the present invention is to propose an orthotopic artificial bladder endoprosthesis that overcomes the above-mentioned technical drawbacks of the known art.

In particular, the aim of the present invention is to provide an orthotopic artificial bladder endoprosthesis that enables a significant reduction in the possibility of post-operative infections.

Another aim of the present invention is to provide an orthotopic artificial bladder endoprosthesis that reduces the risk of stenosis of the patient's ureters.

The specified technical task and the specified aim are substantially achieved by an orthotopic artificial bladder endoprosthesis having the technical characteristics described in one or more of the accompanying claims.

Further characteristics and advantages of the present invention will emerge more clearly from the following non-limiting description of a preferred but not exclusive embodiment of an orthotopic artificial bladder endoprosthesis, as illustrated in the accompanying drawings in which.

Figure 1:
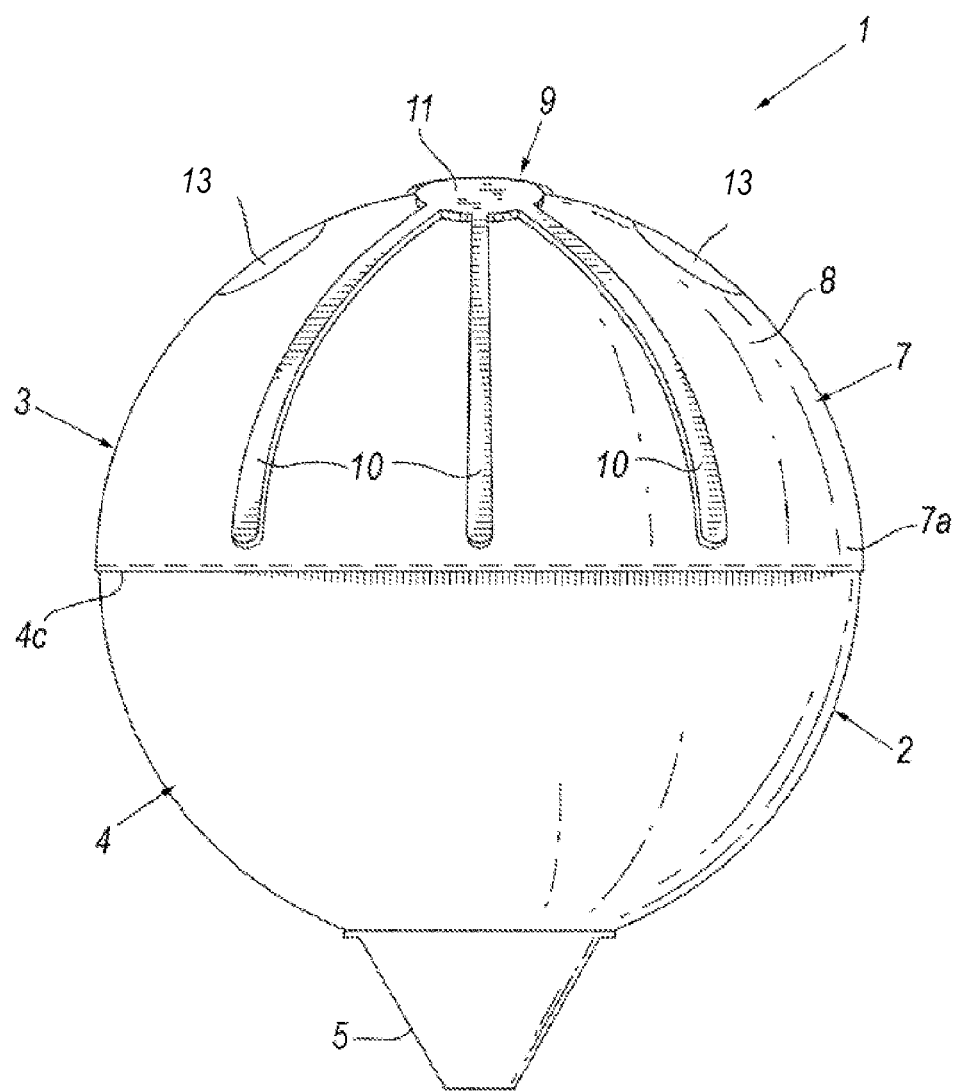
FIG. 1 is a schematic side view of an orthotopic artificial bladder endoprosthesis according to the present invention.
Figure 2:
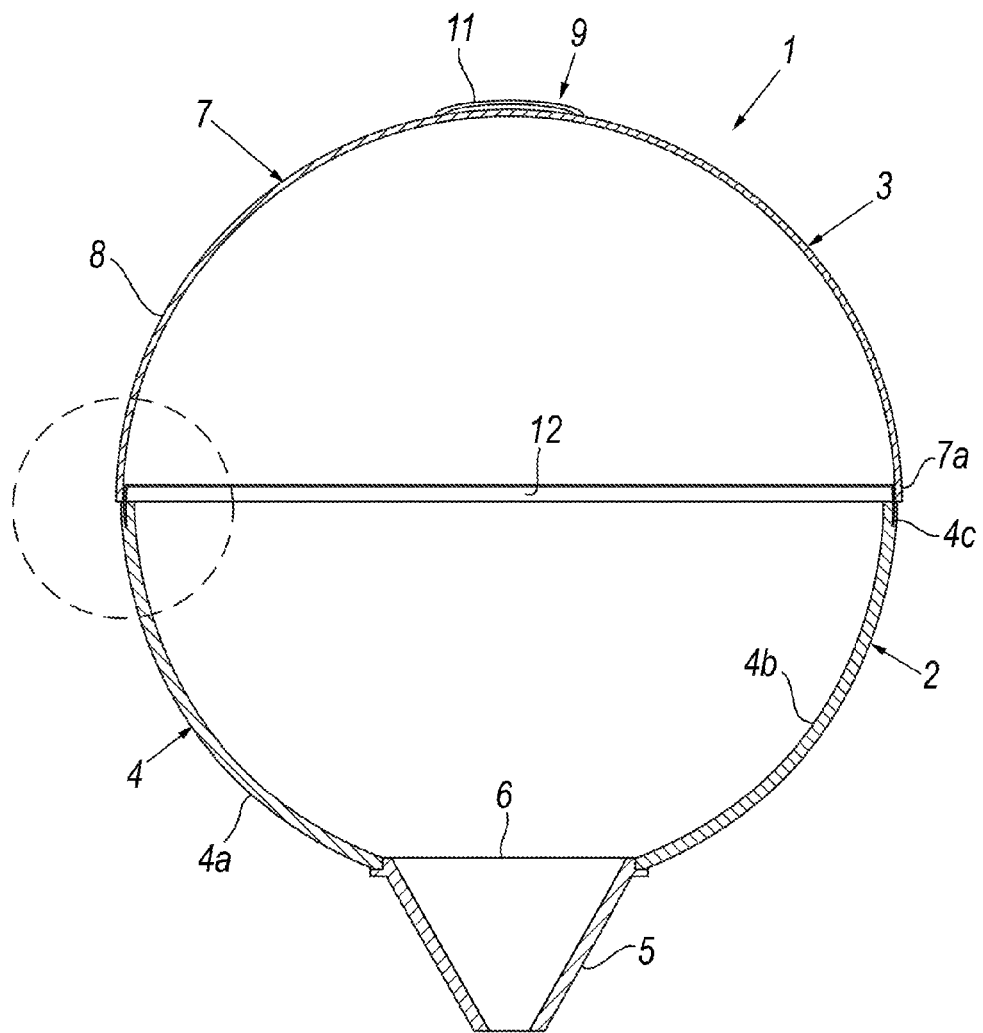
FIG. 2 is a cross-sectional side view of the endoprosthesis shown in FIG. 1.

With reference to the accompanying Figures, 1 indicates an orthotopic artificial bladder endoprosthesis as a whole.

The endoprosthesis 1 comprises a first portion 2 connectable to the urethra of a patient and a second portion 3 connectable to the patient's ureters.

The first 2 and the second portion 3 are different and distinct, but are firmly connected to define a casing inside which is an enclosure to contain the urine. The enclosure has a volume of substantially between 100 cm$^3$ and 900 cm$^3$, preferably being 400 cm$^3$.

In particular, the first portion 2 is of a permanent type, whereas the second portion 3 is of a resorbable type.

More particularly, the first portion 2 comprises a cover 4 made with a multi-layered silicone membrane.

The membrane of the cover 4 is between 500 µm and 700 µm thick, preferably the thickness of the membrane is substantially, 600 µm.

In a preferred embodiment, the membrane substantially comprises 20 layers, each approximately 30 µm thick.

In this way, the cover 4 is therefore sufficiently rigid to maintain its shape, but at the same time sufficiently flexible to be able to be pushed from the outside to promote the expulsion of the urine.

The membrane is produced by means of a process illustrated in Patent Application WO 2007/039159, which is attached hereto for reference.

By way of example, the silicone used may comprise copolymers of dimethyl- and metavinyl-siloxane reinforced with silicon.

Advantageously, the silicone can be admixed with opacifiers such as barium sulphate, titanium dioxide or suchlike, so that the endoprosthesis 1 can be detected by means of radiological diagnostic techniques.

The cover 4 has an external surface 4a and an internal surface 4b.

Both on the external surface 4a and on the internal surface 4b respective layers of a highly biocompatible protective material are applied. By way of example, this material is pyrolytic turbostratic carbon of a thickness of between 0.2 µm and 0.3 µm thick.

The application of the carbon layer on the external surface 4a of the cover 4 allows the risk of the forming fibrous capsule adhering to the first portion 2 to be avoided. The application of the carbon layer on the internal surface 4b of the cover 4 allows the first portion 2 to be protected against the corrosion caused by the urine.

The first portion 2 also comprises a connection body 5 fixed to the cover 4 to enable the connection of the patient's urethra to the endoprosthesis 1.

As illustrated, the connection body 5 has a funnel shape and is glued to the cover 4 at an opening 6 made in the membrane to allow the urine to exit.

In particular, the connection body 5 is glued to the cover 4 at one of its larger bases.

According to a preferred embodiment, the connection body has a height of 15 mm and the larger base of 24 mm. Furthermore, the diameter of the hole in the smaller base is approximately 6 mm and the thickness approximately 1 mm.

The connection body 5 is made of silicone internally reinforced with a net or mesh inserted in the thickness. This net or mesh is made preferably of Dacron® or Goretex®. The connection body 5 is made using known techniques such as, for example, moulding, dipping or suchlike.

The net allows the patient's urethra to be stitched to the connection body 5 in a simpler and more stable way. The second portion 3 comprises a resorbable cap 7 connected to the cover 4. In particular, the cap 7 and the cover 4 are connected along their respective edges 7a, 4c so that the respective concavities are facing each other.

The cap 7 comprises a fabric 8 of a substantially flat circular shape and a frame 9 fixed to the fabric 8. The frame 9 acts as a supporting structure for the fabric 8, enabling it to assume a domed shape which is maintained as such also under the weight of the growth of the fibrous capsule.

The fabric 8 of the cap 7 is made using an ultra-light thread or monofilament deriving from preferably homopolymer PGA (polyglycolide or poylglycolic acid) fibres. PGA is a highly biocompatible and resorbable polymer and resistant to urine. Specifically, the resorption time of PGA is approximately one month.

Advantageously, the use of PGA fibre to make the fabric 8 allows musculo-fibrous tissue to form on the outside of the endoprosthesis 1. Inside, during resorption, we see the formation of a layer of transition epithelium, which is also called urothelium. Advantageously, the layer of urothelium is impermeable, an essential fact to guarantee the correct operation of the prosthesis and the neobladder that is being formed.

The fabric 8 can be obtained by weaving the PGA thread in various ways, giving rise to a knitted fabric, a woven fabric or a non-woven fabric.

Preferably, the fabric 8 is a knitted fabric and, even more preferably, a warp knitted fabric.

In this case, the fabric 8 has a rougher surface capable of assuming a net configuration with sufficiently small links.

More particularly, its weft is such that its interstitial space is less than 200 μm, preferably around 160 μm, corresponding to an average area of the holes of approximately 0.02 mm$^2$. This guarantees impermeability to urine, preventing leaks.

Furthermore, the fabric 8 is preferably textured so as to give it even greater surface roughness and greater rigidity and impermeability. The greater roughness of the fabric limits the risk of adhesion of the fibrous capsule.

Purely by way of example, the fabric 8 has a diameter substantially between 8 mm and 10 mm.

Again purely by way of example, the fabric 8 has a thickness substantially between 0.3 mm and 0.6 mm, more preferably between 0.4 mm and 0.53 mm, even more preferably being substantially 0.45 mm.

On the fabric 8 of the cap 7 there are two interlock areas 13 designed for the connection of the patient's ureters to the endoprosthesis 1. When the endoprosthesis 1 is implanted, the surgeon makes a hole in the cap 7 at the interlock areas 13 to suit the diameter of the ureters.

Note that the position of the interlock areas 13 shown is given purely by way of example.

Specifically, during the operation to implant the endoprosthesis 1, the uereters are connected to the second portion 3 by stitching them to the cap 7 in the interlock areas by means of a resorbable thread.

The frame 9 comprises a plurality of arms 10 arranged in a star and defining a dome profile. More specifically, the arms 10 all have a curved shape and are fixed together at a joining portion 11 located at the top of the cap 7. For example, the frame 9 comprises a plurality of spaced apart radially extending curved arms 10 arranged in a star configuration and defining a dome profile. The arms 10 are fixed together at a joining portion 11 of the frame 9. The fabric 8 of the resorbable cap 7 is connected to the frame 9 so as to assume the dome profile of the frame. The fabric 8 is supported by the frame and extends between the respective arms 10 of the frame 9.

The frame 9 is located outside the cap 7 with reference to the enclosure defined in combination with the cover 4.

In particular, the frame 9 is fixed to the fabric 8 by means of resorbable sutures.

Generally, the thickness of the frame 9, that is, the arms 10 and the joining portion 11, is between 0.1 mm and 10 mm, preferably between 0.5 mm and 2 mm. In a preferred embodiment, the thickness is substantially 1 mm.

The frame 9 is obtained by injection of a copolymer of lactic acid and glycolic acid, indicated as PGA/PLA (poly(lactic-co-glycolic) acid) whose domed shape is imparted when hot by means of thermoforming.

Since lactic acid is a chiral molecule, different types of polymer, PDLA, PLLA, PDLLA exist, where D and L represent the two stereoisomers. PLLA has a crystallinity of 37%, a vitreous transition temperature of between 50° C. and 80° C. and a melting temperature of between 173° C. and 178°, whereas polymer deriving from the polymerisation of a racemic mixture, PDLLA, is amorphous.

The term poly(lactic) acid is here intended to identify all of the various above-mentioned types of PLA.

The PGA/PLA copolymer with which the frame 9 is made is formed by a quantity of PGA of between 20% and 30% and by a quantity of PLA of between, correspondingly, 70% and 80%.

Particularly preferred as a PGA/PLA (poly(lactic-co-glycolic) acid) is the copolymer poly(L-lactic-co-glycolic) (PLLA/PGA) in which the L-lactic acid has a molar percent of 82-88% in moles whereas glycolic acid has a molar percent of 18-12%. This copolymer is commercially known by the name of Resomer® LG855S.

The applicant has surprisingly found that the cap 7 made using the PGA fabric 8 as described above, particularly when textured, in combination with the PGA/PLA frame 9, shows a good mechanical consistency and sufficient rigidity, even in the presence of urine, and so is capable of guaranteeing a correct deformation of the bladder during emptying and/or filling, showing at the same time a good resistance to leaks of urine.

Furthermore, the fabric 8 and the frame 9 have been proved to be neutral when in contact with growing neotissue. This involves a rapid population of the device by the cells of the surrounding growing tissue. At the same time, adhesion has been proved to be reduced due to the reduced interaction between the polymers that comprise the fabric 8 and the frame 9 and the biological molecules, thus guaranteeing a fusion with the patient's internal tissues.

The cover 4 comprises a strip 12 that protrudes from the edge 4c of said cap 4.

In particular, the strip 12 extends along the entire edge 4c of the cover 4.

The strip 12 is made of a biocompatible and preferably non-resorbable material.

The strip 12 is fixed to the cap 7 at the edge 7a. In particular, the strip 12 is fixed along the entire edge 7a of the cap 7.

Preferably, the strip 12 is fixed to the cap 7 by means of stitching made using a resorbable thread. By way of example, this thread may be formed by PGA.

Figure 3:
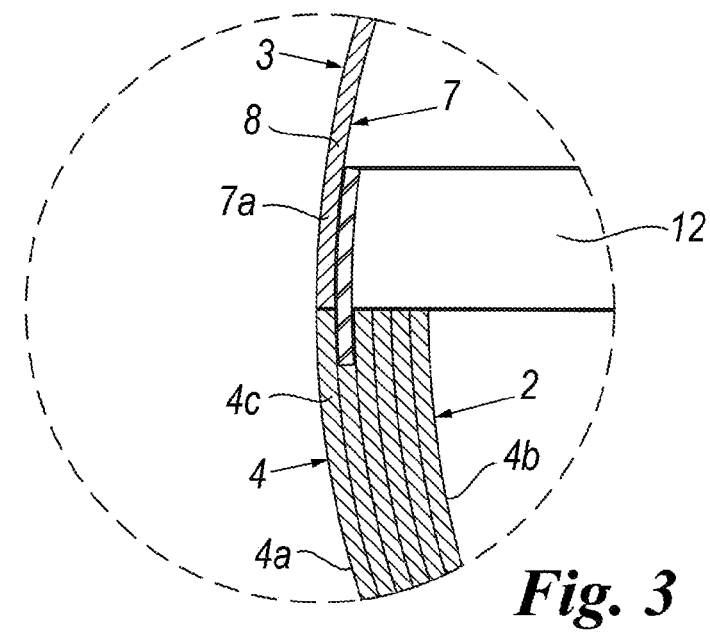
FIG. 3 is a cross-sectional view of a detail of the endoprosthesis shown in FIG. 2.
Figure 4:
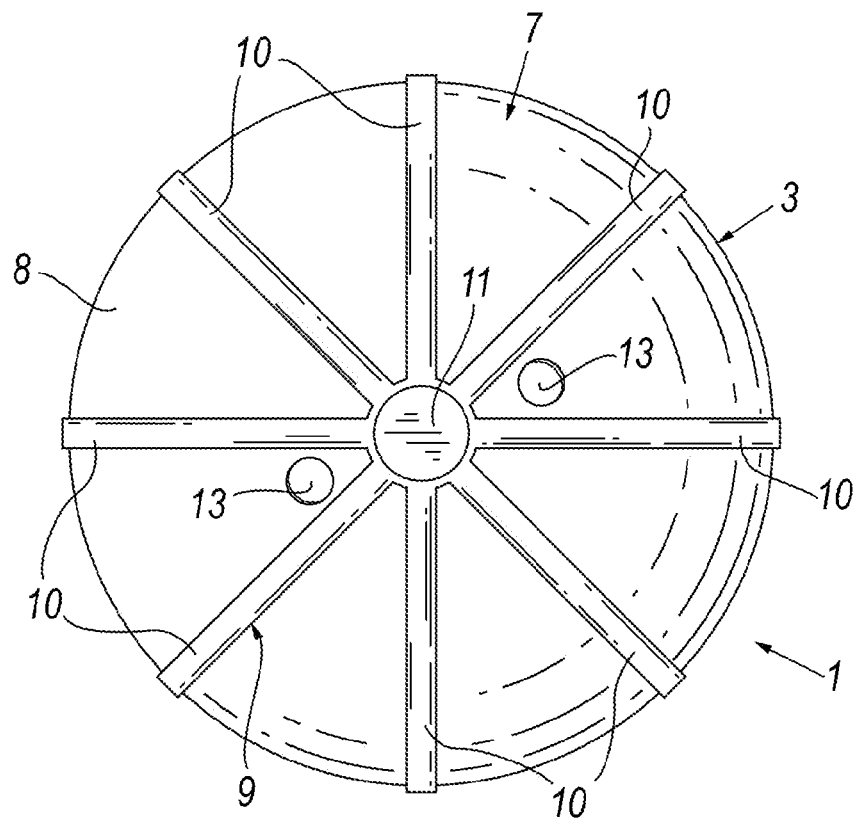
FIG. 4 is a top view of the endoprosthesis shown in FIG. 1.

In the preferred embodiment, the strip 12 is formed by a fabric made of DACRON (i.e. polyethylene terephthalate) and/or GORETEX (i.e. expanded polytetrafluoroethylene). According to that illustrated (FIG. 3), the strip 12 is "embedded" in the membrane that constitutes the cover 4. In other words, the strip 12 is comprised between two adjacent layers of silicone of the membrane. In particular, the strip 12 is positioned between two layers located near the external surface 4a of the cover 4.

The invention thus described achieves the proposed aims. In fact, since the ureters are connected to the resorbable portion, the ureters are gradually welded to the biological tissue of the neobladder forming on the cap.

The connection between the biological material of the ureters and the biological material of the neobladder allows the spread of post-operative infections to be reduced. In fact, the use of antibiotic drugs is effective when the bacterial load is nested on biological rather than artificial tissue. Consequently, the antibiotic drug can act effectively also at the connection between the endoprosthesis and the ureters, preventing the infection from rising.

Furthermore, the connection between ureters and resorbable portion enables a reduction in the risk of stenosis of the ureters.

The invention claimed is:

1. An orthotopic artificial bladder endoprosthesis comprising:
   a first portion connectable to a urethra of a patient and a second portion connectable to ureters of said patient;
   said first portion comprising a collapsible cover made of a multi-layered silicone membrane having an external surface and an internal surface both coated with pyrolytic turbostratic carbon;
   said second portion comprising a resorbable cap comprising a fabric of PGA fibres and a frame, coupled with said cap, made using a PGA/PLA copolymer; said cover and said cap being connected together along respective edges of the cover and of the cap, to define an enclosure between the cover and the cap, the frame comprising a plurality of spaced apart arms, fixed to a joining portion to extend from the joining portion in a star configuration, and defining a dome profile, wherein the frame is disposed over only a portion of the cap such that the fabric of the cap is exposed at each space between adjacent arms of the frame.

2. The endoprosthesis according to claim 1, wherein the cover comprises a strip protruding from said edge of the cover and made of a biocompatible and non-resorbable material; said strip being fixed to said edge of said cap.

3. The endoprosthesis according to claim 2, wherein said strip is formed by a matrix made of polyethylene terephthalate and/or stretched expanded polytetrafluoroethylene.

4. The endoprosthesis according to claim 2, wherein said strip is disposed between two layers located near the respective edge of the cover.

5. The endoprosthesis according to claim 2, wherein said strip extends along the entire edge of the cover.

6. The endoprosthesis according to claim 1, wherein the fabric of said cap is a warp knitted fabric.

7. The endoprosthesis according to claim 1, wherein the copolymer PGA/PLA comprises 30% PGA and 70% PLA.

8. The endoprosthesis according to claim 1, wherein said first portion comprises a connection body connected to the cover to connect said cover to the urethra, said connection body having a substantially funnel shape.

9. The endoprosthesis according to claim 1, wherein the membrane of said cover is between 500 μm and 700 μm thick.

10. The endoprosthesis according to claim 1, wherein the fabric of said cap is a textured fabric.

11. The endoprosthesis according to claim 1, wherein the membrane of said cover is 600 μm thick.

12. An orthotopic artificial bladder endoprosthesis device, comprising:
   a first portion connectable to a urethra of a patient, the first portion comprising a collapsible cover made of a multi-layered silicone membrane having an external surface and an internal surface both coated with pyrolytic turbostratic carbon; and
   a second portion connectable to ureters of said patient, the second portion comprising:
      a resorbable cap comprising a fabric of PGA fibres; and
      a frame connected to the fabric of the cap, the frame comprising a plurality of spaced apart curved arms arranged in a star configuration and defining a dome profile, the arms are fixed together at a joining portion of the frame to extend from the joining portion, the frame being made using a PGA/PLA copolymer; and
   an edge of the cover and an edge of the cap connected at an edge connection to form an enclosure between the cover and the cap, the edge connection comprising a strip of material protruding from the edge of the cover and embedded between two adjacent silicone layers of the membrane, thereby providing a protruding edge of the cover at which the cap is connected;
   wherein the fabric of the resorbable cap is connected to the frame to assume the dome profile of the frame, and
   wherein the fabric of the resorbable cap is supported by the frame.

13. The device according to claim 12, wherein the frame is fixed to the fabric of the cap by one or more resorbable devices.

14. The device according to claim 12, wherein the one or more resorbable devices is resorbable sutures.

15. The device according to claim 12, wherein the dome profile of the frame is imparted when hot by thermoforming.

16. The device according to claim 12, wherein the frame is located outside of the cap.

* * * * *